United States Patent
Okada et al.

(10) Patent No.: US 10,188,767 B2
(45) Date of Patent: Jan. 29, 2019

(54) SCENT PRESENTATION METHOD, SCENT PRESENTATION APPARATUS, AND OLFACTION IMPROVING APPARATUS

(71) Applicant: KEIO UNIVERSITY, Tokyo (JP)

(72) Inventors: Kenichi Okada, Kanagawa (JP); Sho Kanzaki, Tokyo (JP); Shohei Horiguchi, Kanagawa (JP)

(73) Assignee: KEIO UNIVERSITY, Tokyo (JP)

( * ) Notice: Subject to any disclaimer, the term of this patent is extended or adjusted under 35 U.S.C. 154(b) by 207 days.

(21) Appl. No.: 15/193,452

(22) Filed: Jun. 27, 2016

(65) Prior Publication Data

US 2016/0379506 A1  Dec. 29, 2016

(30) Foreign Application Priority Data

Jun. 29, 2015 (JP) ................................. 2015-130118

(51) Int. Cl.
| | |
|---|---|
| *A61L 9/00* | (2006.01) |
| *G09B 19/00* | (2006.01) |
| *A61B 5/00* | (2006.01) |
| *G09B 5/06* | (2006.01) |
| *G09B 7/06* | (2006.01) |
| *A61L 9/12* | (2006.01) |
| *A61L 9/14* | (2006.01) |

(52) U.S. Cl.
CPC .............. *A61L 9/00* (2013.01); *A61B 5/4011* (2013.01); *A61L 9/122* (2013.01); *A61L 9/14* (2013.01); *G09B 5/06* (2013.01); *G09B 7/06* (2013.01); *G09B 19/00* (2013.01); *A61L 2209/11* (2013.01); *A61L 2209/12* (2013.01); *A61L 2209/132* (2013.01); *A61L 2209/133* (2013.01)

(58) Field of Classification Search
CPC .................................................. A61B 5/4011
See application file for complete search history.

(56) References Cited

U.S. PATENT DOCUMENTS

| | | | | |
|---|---|---|---|---|
| 5,918,882 | A * | 7/1999 | Truong | A63F 3/0478 273/249 |
| 2002/0002076 | A1 * | 1/2002 | Schneier | A63F 13/12 463/29 |
| 2003/0223040 | A1 * | 12/2003 | Schermerhorn | G03B 21/00 352/85 |
| 2014/0051045 | A1 * | 2/2014 | Stults | G09B 19/00 434/236 |
| 2014/0094268 | A1 * | 4/2014 | Adams | G07F 17/3267 463/21 |

(Continued)

FOREIGN PATENT DOCUMENTS

JP  2014-219644  11/2014

OTHER PUBLICATIONS

Machine Translation of JP2014-219644 (English) accessed and translated from Espacenet on Mar. 17, 2018.*

(Continued)

*Primary Examiner* — Jason Skaarup
(74) *Attorney, Agent, or Firm* — IPUSA, PLLC

(57) ABSTRACT

A scent presentation method is provided that includes generating a random number, determining a presentation condition based on the generated random number, and presenting a scent through pulse ejection based on the determined presentation condition.

8 Claims, 9 Drawing Sheets

(56) References Cited

U.S. PATENT DOCUMENTS

2014/0377130 A1* 12/2014 Edwards .................. A61L 9/02
422/5
2015/0048178 A1* 2/2015 Edwards ................ A61L 9/032
239/13

OTHER PUBLICATIONS

Wendy V. Parr et al.: Demystifying Wine Expertise: Olfactory Threshold, Perceptual Skill and Semantic Memory in Expert and Novice Wine Judges; Chem. Senses (Jul. 2002) 27 (8), pp. 747-755.

* cited by examiner

FIG.9A

| | 1ST | 2ND | 3RD | 4TH |
|---|---|---|---|---|
| BANANA | UNMEASURABLE | UNMEASURABLE | UNMEASURABLE | UNMEASURABLE |
| MINT | UNMEASURABLE | UNMEASURABLE | 0.23 | 0.20 |
| LAVENDER | UNMEASURABLE | UNMEASURABLE | 0.17 | 0.17 |
| ROSE | UNMEASURABLE | UNMEASURABLE | 0.17 | UNMEASURABLE |

FIG.9B

| | 1ST | 2ND | 3RD | 4TH |
|---|---|---|---|---|
| BANANA | 0.43 | 0.39 | 0.30 | 0.23 |
| MINT | 0.19 | 0.13 | 0.06 | 0.08 |
| LAVENDER | 0.11 | 0.06 | 0.04 | 0.04 |
| ROSE | 0.08 | 0.08 | 0.08 | 0.04 |

FIG.9C

| | 1ST | 2ND | 3RD |
|---|---|---|---|
| BANANA | UNMEASURABLE | 0.69 | 0.56 |
| MINT | UNMEASURABLE | 0.21 | 0.19 |
| LAVENDER | UNMEASURABLE | 0.21 | 0.15 |
| ROSE | UNMEASURABLE | UNMEASURABLE | UNMEASURABLE |

FIG.9D

| | 1ST | 2ND | 3RD | 4TH |
|---|---|---|---|---|
| BANANA | 0.033 | 0.066 | 0.066 | 0.044 |
| MINT | 0.042 | 0.063 | 0.056 | 0.028 |
| LAVENDER | 0.021 | 0.021 | 0.042 | 0.028 |
| ROSE | 0.063 | 0.085 | 0.014 | 0.042 |

FIG.9E

| | 1ST | 2ND | 3RD | 4TH |
|---|---|---|---|---|
| BANANA | 0.022 | 0.022 | 0.022 | 0.033 |
| MINT | 0.014 | 0.021 | 0.021 | 0.007 |
| LAVENDER | 0.014 | 0.007 | 0.007 | 0.007 |
| ROSE | 0.042 | 0.035 | 0.028 | 0.035 |

SCENT PRESENTATION METHOD, SCENT PRESENTATION APPARATUS, AND OLFACTION IMPROVING APPARATUS

CROSS-REFERENCE TO RELATED APPLICATION

The present application is based on and claims the benefit of priority to Japanese Patent Application No. 2015-130118 filed on Jun. 29, 2015, the entire contents of which are hereby incorporated by reference.

BACKGROUND OF THE INVENTION

1. Field of the Invention

The present invention relates to a scent presentation method, a scent presentation apparatus, and an olfaction improving apparatus for presenting a scent through pulse ejection.

2. Description of the Related Art

The human sense of smell (olfactory sense) is indispensable for detecting dangers and the like in everyday life, such as the odor of an oil stove, the odor of a gas leak, a burning odor from a fire, or the odor of spoiled food, for example.

It is known that olfactory capabilities of humans of the modern age are gradually declining due to aging or improved environmental sanitation, for example. Further, an overall wellness or decline in health of a person can be determined based on the olfactory capabilities of that person.

Thus, the sense of smell is important in various fields for realizing a safe and prosperous living environment in modern society.

In recent years, scent presentation methods and scent presentation apparatuses for stimulating the human olfactory capabilities are subject to research and development. For example, a technique is known for ejecting a plurality of different types of scents through pulse ejection in a predetermined order over a designated period through computer control (see, e.g., Japanese Laid-Open Patent Publication No. 2014-219644).

Note that pulse ejection of a scent refers to the ejection of scents at short time intervals.

According to recent reports, a decline in olfactory capabilities may appear as early symptoms of diseases such as Alzheimer-type dementia. It is desirable to prevent such decline in olfactory capabilities to enable continued engagement in various hobbies and entertainment involving olfaction, for example.

One example study has been conducted that suggests a method of improving olfactory capabilities. In this study, the olfactory capabilities of wine experts who habitually make conscious efforts to smell odors were compared with the olfactory capabilities of wine novices (see Wendy V. Parr et al.: Demystifying Wine Expertise: Olfactory Threshold, Perceptual Skill and Semantic Memory in Expert and Novice Wine Judges; Chem. Senses (July 2002) 27 (8), pp. 747-755). In this study, an experiment was conducted where two groups of scents each consisting of various spices and fruits were sequentially presented to the participants after which the participants were asked to determine whether a scent included in the second group was also included in the first group. The results of the experiment revealed that the olfactory recognition capabilities of the wine experts were superior to those of the wine novices. The above findings suggest that habitually making a conscious effort to smell odors can lead to improvement of olfactory capabilities.

Thus, there is a demand for a scent presentation method and a scent presentation apparatus for improving, maintaining, and enhancing olfactory capabilities.

Note that while techniques are known for presenting a scent to a user through pulse ejection for the purpose of preventing the user from becoming adapted to the scent, these techniques are not suited for effectively improving, maintaining, and enhancing olfactory capabilities of the user.

SUMMARY OF THE INVENTION

According to one aspect of the present invention a scent presentation method, a scent presentation apparatus, and an olfaction improving apparatus are provided for improving, maintaining, and enhancing olfactory capabilities.

According to one embodiment of the present invention, a scent presentation method is provided that includes generating a random number, determining a presentation condition based on the generated random number, and ejecting a scent through pulse ejection based on the determined presentation condition.

According to another embodiment of the present invention, a scent presentation apparatus is provided that includes an ejection unit configured to eject a scent through pulse ejection, and a control unit configured to control the pulse ejection of the scent by the ejection unit based on a presentation condition that is determined by a random number generated randomly.

According to another embodiment of the present invention, an olfaction improving apparatus is provided that includes an information processing apparatus including a random number generating unit configured to generate a random number and an arithmetic processing unit configured to determine a presentation condition based on the random number generated by the random number generating unit, a scent presentation apparatus including a control unit configured to control ejection of a scent through pulse ejection based on the determined presentation condition, and a display terminal configured to display an image associated with the scent on a display screen.

BRIEF DESCRIPTION OF THE DRAWINGS

FIGS. 9A-9E are tables indicating results of performing the olfactory improving treatment on patients 1 to 5.

DESCRIPTION OF THE PREFERRED EMBODIMENTS

In the following, embodiments of the present invention are described with reference to the accompanying drawings.

Overall Configuration

Figure 1:
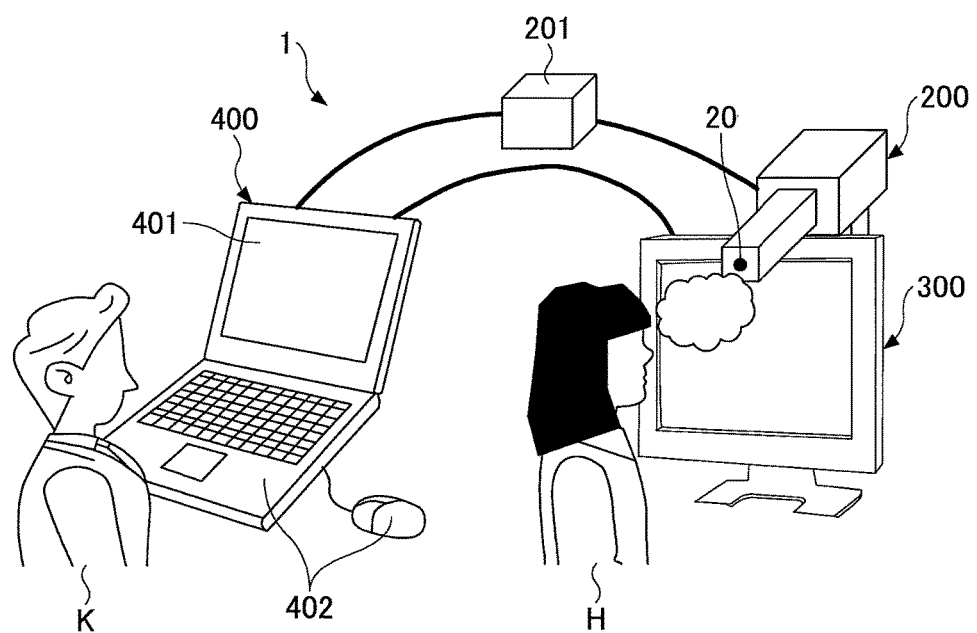
FIG. 1 is a conceptual diagram showing an olfaction improving apparatus that implements a scent presentation method according to an embodiment of the present invention.

FIG. 1 is a conceptual diagram showing an overall configuration of an olfaction improving apparatus 1 that implements a scent presentation method according to an embodiment of the present invention.

The olfaction improving apparatus 1 includes a scent presentation apparatus 200 for presenting a plurality of scents to a user H through pulse ejection, a tablet terminal 300 (as an example of a display terminal) for displaying an image associated with the scent being presented on a display screen, and an information processing apparatus 400 for controlling the scent presentation apparatus 200 and the tablet terminal 300.

The scent presentation apparatus 200 presents a plurality of scents to the user H through pulse ejection. In the present example, the scent presentation apparatus 200 is an olfactory display called "FJMC (Fragrance Jet for Medical Checkup)". The scent presentation apparatus 200 stores a plurality of types of scents and is configured to present the scents through pulse ejection. Specifically, the scents are stored in a plurality of tanks that are installed in the scent presentation apparatus 200, and ejection technology for inkjet printers is used to eject the scents. The scent presentation apparatus 200 is a highly precise and sophisticated apparatus that is capable of switching the ejection quantity and/or the type of scent within a very short time, ejecting a scent through pulse ejection, and reducing the effects of lingering scents and adaptation to scent. Also, the scent presentation apparatus 200 is preferably a demountable unit. Note that the scent presentation apparatus 200 shown in FIG. 1 has a control unit 210 that is provided outside a main body of the scent presentation apparatus 200. In this way, the size of the main body of the scent presentation apparatus 200 may be reduced. However, the control unit 210 may also be arranged inside the main body of the scent presentation apparatus 200.

The tablet terminal 300 is a terminal apparatus including a liquid crystal flat screen or the like. The tablet terminal 300 may be a smartphone, for example. The tablet terminal 300 may include an input unit, a display unit, an audio generating unit, an external I/F (interface), a RAM (storage unit), a ROM (storage unit), a CPU, a communication I/F, and a HDD (hard disk drive), for example. In some embodiments, the tablet terminal 300 may be a so-called wearable device that can be attached to the body, for example.

The information processing apparatus 400 may be a PC (personal computer) or the like that is operated by an administrator K. The information processing apparatus 400 includes an output unit 401, such as a monitor, and an input unit 402, such as a mouse and a keyboard.

The scent presentation apparatus 200 and the tablet terminal 300 are electrically connected to the information processing apparatus 400. The information processing apparatus 400 transmits a control signal to the scent presentation apparatus 200 for presenting a scent through pulse ejection.

The information processing apparatus 400 transmits a control signal to the tablet terminal 300 for displaying an image associated with the scent being presented, and guidance information for performing various operations on the tablet terminal 300.

Figure 2:
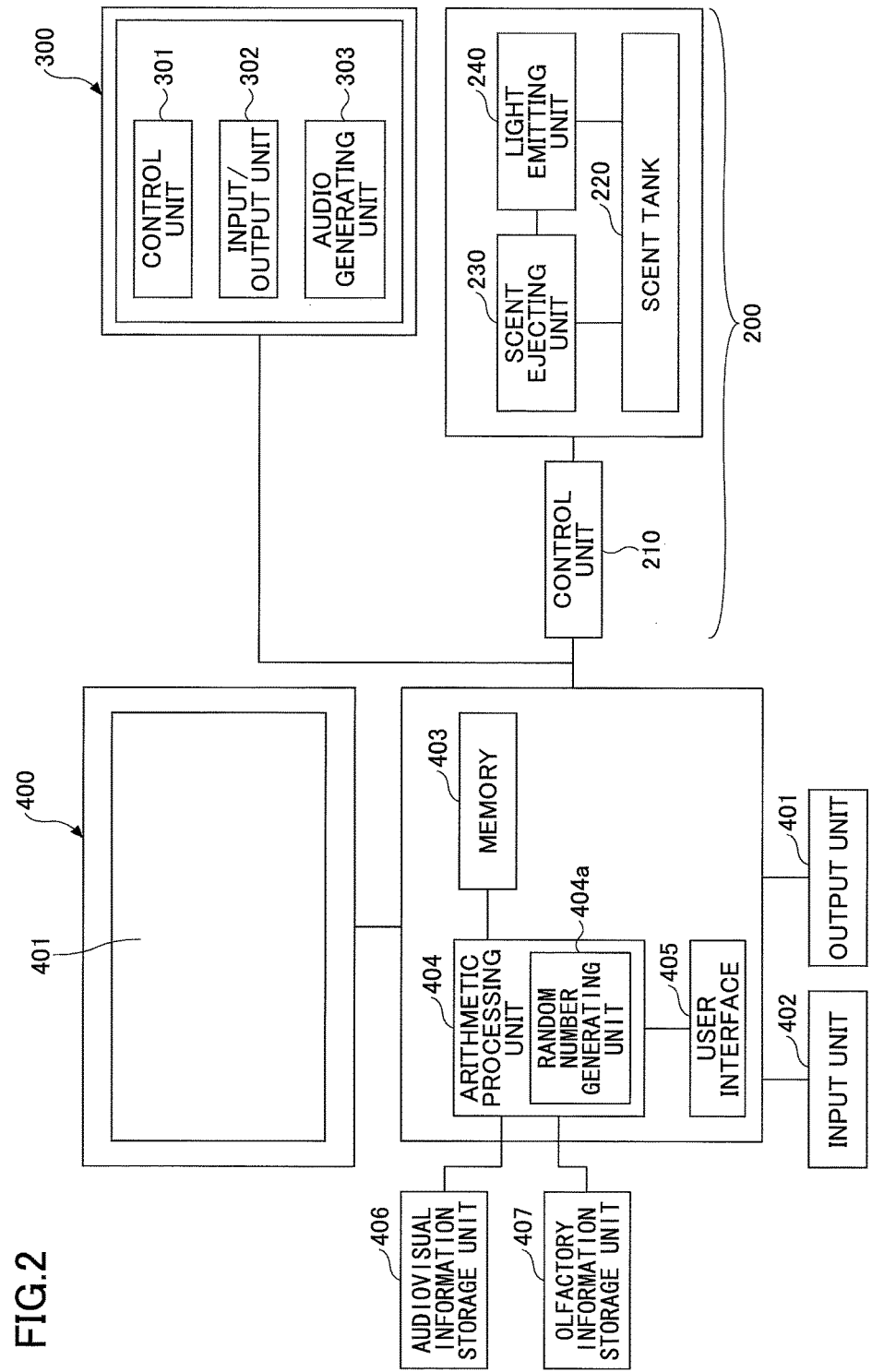
FIG. 2 is a diagram showing a system configuration of the olfaction improving apparatus that implements the scent presentation method according to an embodiment of the present invention.

FIG. 2 is a block diagram showing an example system configuration of the olfaction improving apparatus that implements the scent presentation method according to an embodiment of the present invention.

The information processing apparatus 400 includes a memory 403, an arithmetic processing unit (control unit) 404, a user interface 405, an audiovisual information storage unit 406, and an olfactory information storage unit 407. The information processing apparatus 400 also includes an output unit 401, such as a printer and/or a monitor, and an input unit 402, such as a mouse and/or a keyboard. The arithmetic processing unit 404 executes processes for implementing the scent presentation method according to the present embodiment. That is, the arithmetic processing unit 404 executes processes, such as determining a presentation condition for ejecting a scent, transmitting the presentation condition to the scent presentation apparatus 200, and transmitting a control signal for presenting an image (and/or audio) associated with the scent to be presented by the scent presentation apparatus 200 to the tablet terminal 300. Note that in the present embodiment, the presentation condition corresponds to "type of scent". Other examples of presentation conditions include "intensity of scent", "pulse ejection time", and "pulse ejection interval before a next scent ejection" (hereinafter simply referred to as a "pulse ejection interval"), and the like.

As described in detail below, the arithmetic processing unit 404 according to the present embodiment implements a function of randomly determining a presentation condition for presenting a scent based on a random number. As such, the processing unit 404 includes a random number generating unit 404a. The random number generating unit 404a has a function of generating a random number. In the present embodiment, a random number generated by the random number generating unit 404a is an integer.

Note that in some embodiments, the arithmetic processing unit 404 may be configured to determine whether to display an image (and/or audio) associated with the scent to be presented as a presentation condition, for example. That is, the arithmetic processing unit 404 may determine whether to control the tablet terminal 300 to display an image (and/or audio) associated with the scent to be ejected based on the random number generated by the random number generating unit 404a, for example. In this way, for example, in a case where the olfactory capabilities of a user appears to have improved, the degree of improvement of the user's olfactory capabilities may be determined by presenting a scent without an image and/or audio associated with the scent.

The audiovisual information storage unit 406 stores image information and/or audio information associated with the scent to be presented. For example, with respect to the presentation condition "type of scent", image information and/or audio information may be stored in association with each type element (selection element), such as "banana", "mint", "lavender", or "rose", provided as an option for the "type of scent". For example, with respect to the type element "banana", an image of bananas and audio information of a voice saying "bananas" may be stored.

The scent information storage unit 407 stores information relating to presentation conditions, such as "type of scent", "intensity of scent", "pulse ejection time", and "pulse ejection interval", and other various information relating to scents, for example.

The tablet terminal 300 includes a control unit 301, an input/output unit 302, and an audio generating unit 303. The control unit 301 controls the input/output unit 302 to display image information associated with a scent transmitted from the information processing apparatus 400 on a display screen. The control unit 301 also controls the audio generating unit 303 to generate audio information associated with a scent transmitted from the information processing apparatus 400. The control unit 301 also controls the input/output unit 302 to display guidance information transmitted from the information processing apparatus 400 on a display screen. The guidance information may include various information items, such as information prompting a user to input an instruction to start scent presentation, information prompting the user to indicate whether the user has recognized the scent, information prompting the user to indicate whether to proceed to a next scent, and the like.

The input/output unit 302 may be a touch panel, for example. The input/output unit 302 has the function of displaying an image on a monitor and the function of accepting a touch operation performed on the monitor. The audio generating unit 303 may be a speaker, for example. In the present embodiment, in contemplation of potential users that may be visually impaired, the tablet terminal 300 is preferably configured to generate audio associated with a scent, such as a voice saying "bananas", via the audio generating unit 303 in addition to displaying an image associated with the scent, such as an image of bananas, on the touch panel 302. This may be accomplished by storing corresponding image information and audio information associated with each type element (selection element) provided as an option for the "type of scent" corresponding to one example of a presentation condition as described above. Also, in some embodiments, audio information notifying the presentation timing of the scent may be generated.

The scent presentation apparatus 200 includes the control unit 210, a scent tank 220, a scent ejecting unit 230, and a light emitting unit 240.

The control unit 210 controls the scent ejecting unit 230 to eject a scent stored in the scent tank 220 based on one or more presentation conditions determined by a random number transmitted from the information processing apparatus 400, for example.

The scent tank 220 is capable of storing a scent. Applying inkjet printer technology to scent presentation, the scent tank 220 is set up in a cartridge.

The cartridge preferably accommodates two types of tanks including a large tank and a small tank, for example. By installing two types of tanks including a large tank and a small tank in the cartridge, the amount of scent being ejected may be easily controlled, for example. Note that in some embodiments only small tanks may be installed in the cartridge. In this way, more types of scents may be presented, for example. The cartridge is capable of accommodating a plurality of tanks storing different scents, and different combinations of the scents may be ejected.

The scent ejecting unit 230 is an example of an ejection unit that ejects a scent through pulse ejection using inkjet printer technology. For example, the scent ejecting unit 230 may use a Bubble Jet (trade name) head that emits a scent in liquid form into the air from minute holes formed at the bottom of the tanks. The scent ejecting unit 230 may also use a piezo head, for example.

In the present descriptions, "pulse ejection" refers to ejecting a scent over one waveform component of a pulse wave (rectangular wave) generated for presenting a scent.

In the present embodiment, the large tank has 255 minute holes and the small tank has 128 minute holes. By controlling the number of holes from which a scent is to be simultaneously ejected and the pulse ejection time, the ejection quantity of a scent from each tank may be dynamically adjusted to 256 different levels (0-255) for the large tank or 128 different levels (0-127) for the small tank. The ejection quantity can be calculated by the following equation (1).

$$\text{Ejection Quantity (pL)} = \text{Unit Average Ejection Quantity (pL/(number*sec))} \times \text{Number of Simultaneous Ejections (number)} \times \text{Pulse Ejection Time (sec)} \quad (1)$$

Note that "Unit Average Ejection Quantity" refers to the average ejection quantity from each minute hole, "Number of Simultaneous Ejections" refers to the number of minute holes ejecting a scent at the same time. In the present embodiment, "intensity of scent" corresponds to the number of simultaneous ejections (height of pulse waveform). Also, in the present embodiment, "pulse ejection time" refers to the time during which a scent is ejected (width of pulse waveform). Thus, the ejection quantity may be determined by determining the "intensity of scent" and the "pulse ejection time".

The scent ejecting unit 230 is capable of switching the intensity of scent and the type of scent every 100 ms (milliseconds). The pulse ejection time can be set up in units of 100 ms (e.g., 100 ms, 200 ms, or 300 ms), and further, a number between 1 and 150 may be set up as the number of continuous pulse ejection time units over which a scent is to be continuously ejected within the 100-ms pulse ejection time.

Thus, the minimum pulse ejection time that can be set up for the scent ejecting unit 230 is 667 μs (microseconds), which is obtained by dividing 100 ms by 150. That is, the number of continuous pulse ejection time units may be set to 1 to obtain a pulse ejection time of 667 μs, and the number of continuous pulse ejection time units may be set to 150 to obtain a pulse ejection time of 100 ms. Note that in the present embodiment, the ejection time is adjusted to be in the range of about 100-300 ms.

The light emitting unit 240 (corresponding to an example of an ejection notification unit) may be an LED element that is provided at the outer peripheral surface of the control unit 210, for example. The light emitting unit 204 may also be provided at the outer peripheral surface of the scent presentation apparatus 200, for example. The LED element may be configured to emit light at the time a scent is being ejected. The color of the LED element may be set up for each tank to enable visual determination of whether a scent is being properly ejected from a designated tank, for example.

The scent presentation apparatus 200 having the above-described configuration may have a fan installed at its rear side (opposite side of the ejecting direction) such that a scent being ejected may be blown toward an ejection port 20 (see FIG. 1) by a wind generated by the fan. The fan can be adjusted to generate a wind at 10 different velocities (0-9). Also, a nozzle may be attached to the ejection port 20, and medical equipment, such as a nose piece, may be attached to the nozzle as necessary or desired. Note that in some embodiments, an inkjet head with a piezoelectric element may be used for ejecting a scent, for example.

<Scent Presentation Method>

Figure 3:
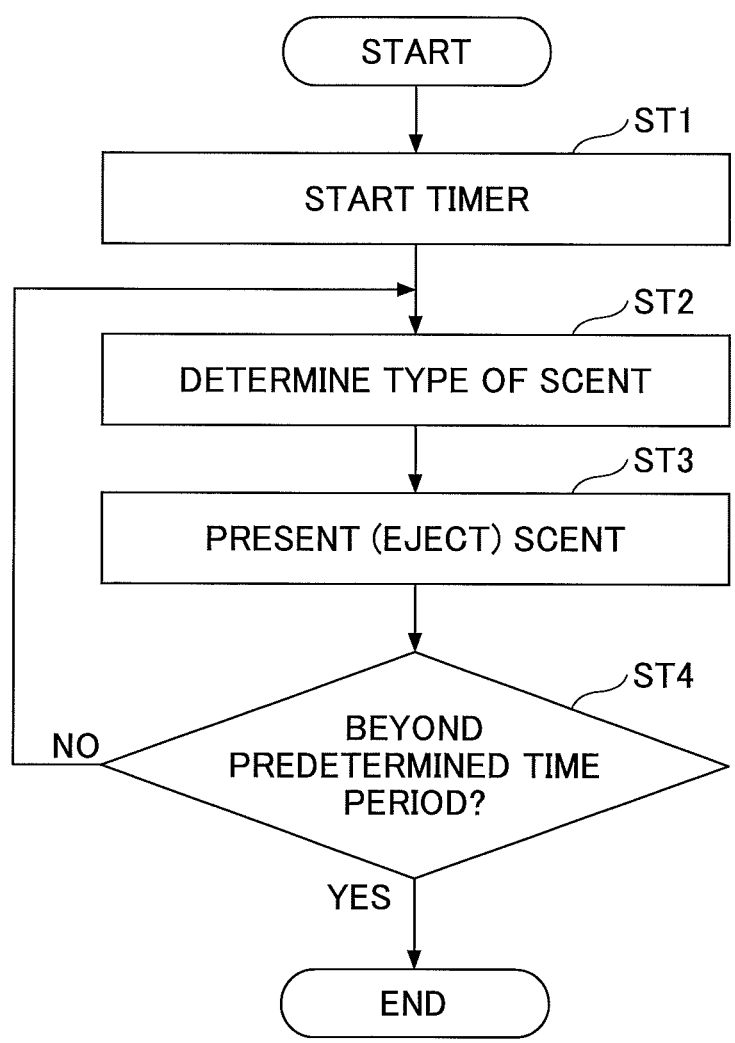
FIG. 3 is a flowchart showing an example process flow of the scent presentation method according to an embodiment of the present invention.

In the following, a scent presentation method according to an embodiment of the present invention is described. FIG. 3 is a flow chart showing an example process flow of a scent presentation method implemented by the olfaction improving apparatus 1 including the scent presentation apparatus 200 as described above. Note that in the following descriptions, it is assumed that a scent is repeatedly presented (ejected) for a predetermined time period.

In step ST1, the arithmetic processing unit 404, acting as a timer, starts counting to a predetermined time period (e.g., 5 minutes), which is set up in advance as a scent presentation period. The timer may be started by a user touching a start button that is displayed on the touch panel of the tablet terminal 300, for example. Note that although a predetermined time period is set up as the scent presentation period in the above example, in other examples, a number of times a given scent is to be presented may be set up as a parameter for defining the scent presentation period, for example.

Then, in step ST2, the arithmetic processing unit 404 determines the presentation condition "type of scent". Note that in the scent presentation method according to the present embodiment, when determining a presentation condition, the random number generating unit 404a of the information processing apparatus 400 generates a random number, and the presentation condition is randomly determined based on the generated random number.

In the following, specific procedures of step ST2 are described with reference to FIG. 4.

Figure 4:
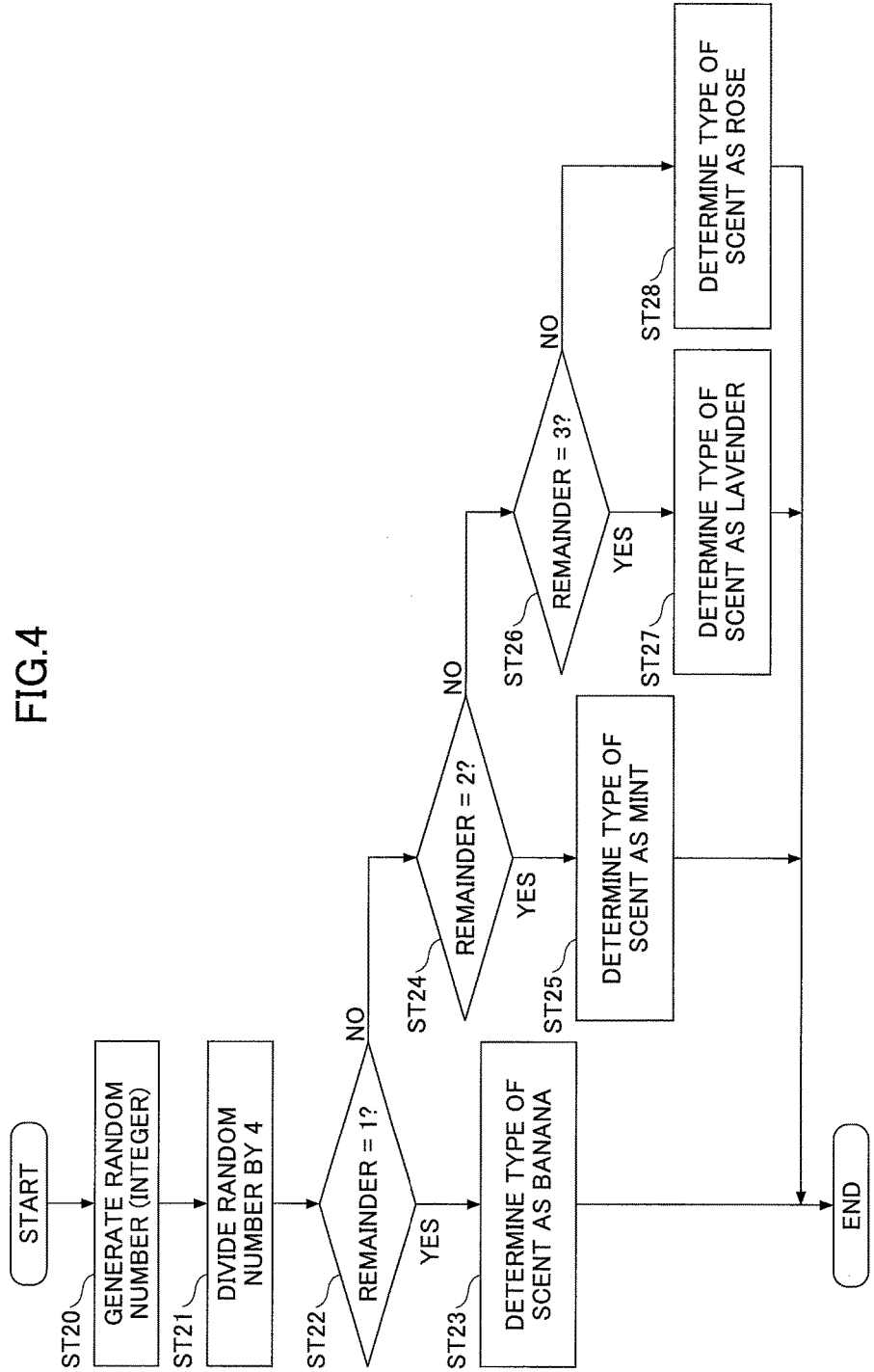
FIG. 4 is a flowchart showing an example process for determining a type of scent using a random number.

FIG. 4 is a flowchart showing an example process for randomly determining the "type of scent" based on a random number. In the example of FIG. 4, four selection elements are provided as options for the presentation condition "type of scent".

In step ST20, the arithmetic processing unit 404 of the information processing apparatus 400 controls the random number generating unit 404a to generate a random number. In the present example, the random number to be generated may be any integer.

Then, in step ST21, the arithmetic processing unit 404 divides the generated random number by the number of selection elements that are provided as options for the "type of scent" (i.e., "4" in the present example). Note that in the present example, four selection elements including "banana", "mint", "lavender", and "rose" are provided as options for the "type of scent".

Then, in step ST22, the arithmetic processing unit 404, determines whether the remainder after dividing the random number by "4" is "1". If the remainder is "1" (YES in step ST22), the arithmetic processing unit 404 proceeds to step ST23 where it determines the "type of scent" as "banana" and terminates the determination process.

If it is determined in step ST22 that the remainder is not "1" (NO in step ST22), the arithmetic processing unit 404 proceeds to step ST24 where it determines whether the remainder is "2". If the remainder is "2" (YES in step ST24), the arithmetic processing unit 404 proceeds to step ST25 where it determines the "type of scent" as "mint" and terminates the determination process.

If it is determined in ST24 that the remainder is not "2" (NO in step ST24), the arithmetic processing unit 404 proceeds to step ST26 where it determines whether the remainder is "3". If the remainder is "3" (YES in step S26), the arithmetic processing unit 404 proceeds to step ST27 where it determines the "type of scent" as "lavender" and terminates the determination process. If it is determined in step ST26 that the remainder is not "3" (i.e., if the remainder is "0"), the arithmetic processing unit 404 proceeds to step ST28 where it determines the "type of scent" as "rose", and terminates the determination process.

To implement the above process steps, the remainder values are associated with corresponding selection elements. That is, in the above example, "banana" is selected if the remainder is "1", "mint" is selected if the remainder is "2", "lavender" is selected if the remainder is "3", and "rose" is selected if the remainder is a value other than 1-3. In this way, the presentation condition "type of scent" can be randomly selected based on a random number that has been generated. Also, in the present embodiment, the selection elements for the "type of scent" are associated with corresponding images, and in this way, the tablet terminal 300 can display an image associated with the selected scent.

Referring back to FIG. 3, when the "type of scent" is determined by the process steps of FIG. 4, the process proceeds to step ST3 where the arithmetic processing unit 404 controls the scent presentation apparatus 200 to present (eject) the determined type of scent to the user H.

For example, if "banana" is designated as the "type of scent", a corresponding banana scent (isoamyl acetate) is ejected from the scent ejecting unit 230 of the scent presentation apparatus 200 through pulse ejection. Also, an image of bananas is displayed on the input/output unit 302 (touch panel) of the tablet terminal 300. Further, audio of a voice saying "bananas" or the like may be generated by the audio generating unit 303. Also, in some embodiments, audio information notifying the scent presentation timing may be generated in addition to the above information on the type of scent, for example. Note that the audio information to be generated may be designated in advance or the user may be able to select the desired audio information, for example.

After the determined type of scent is presented to the user in step ST3, the arithmetic processing unit 404 proceeds to step ST4 where it determines whether the predetermined time period (e.g., 5 minutes) has elapsed. If the predetermined time period has not yet elapsed (NO in step ST4), the arithmetic processing unit 404 returns to step ST2, and repeats the determination process to determine the next "type of scent" to be presented to the user H. If the predetermined time period has elapsed (YES in step ST4) the scent presentation process is ended.

Note that in the example of FIG. 3, presentation conditions, such as "intensity of scent", "pulse ejection time", and "pulse ejection interval", are designated in advance, and the scent presentation process is performed based on the pre-designated values set up for these presentation conditions.

However, the presentation conditions, such as "intensity of scent", "pulse ejection time", and "pulse ejection interval", may also be randomly determined based on a random number.

In the following, referring to FIG. 5, a scent presentation method that involves randomly determining a plurality of presentation conditions based on a random number is described.

In step ST30, the arithmetic processing unit 404 starts counting to a predetermined time period (e.g., 5 minutes) that is set up in advance as the scent presentation period. Then, in step ST31, the arithmetic processing unit 404 determines the "type of scent" corresponding to one of the presentation conditions. Note that the "type of scent" may be determined by the determination process as shown in FIG. 4, and as such, descriptions thereof are omitted.

Figure 5:
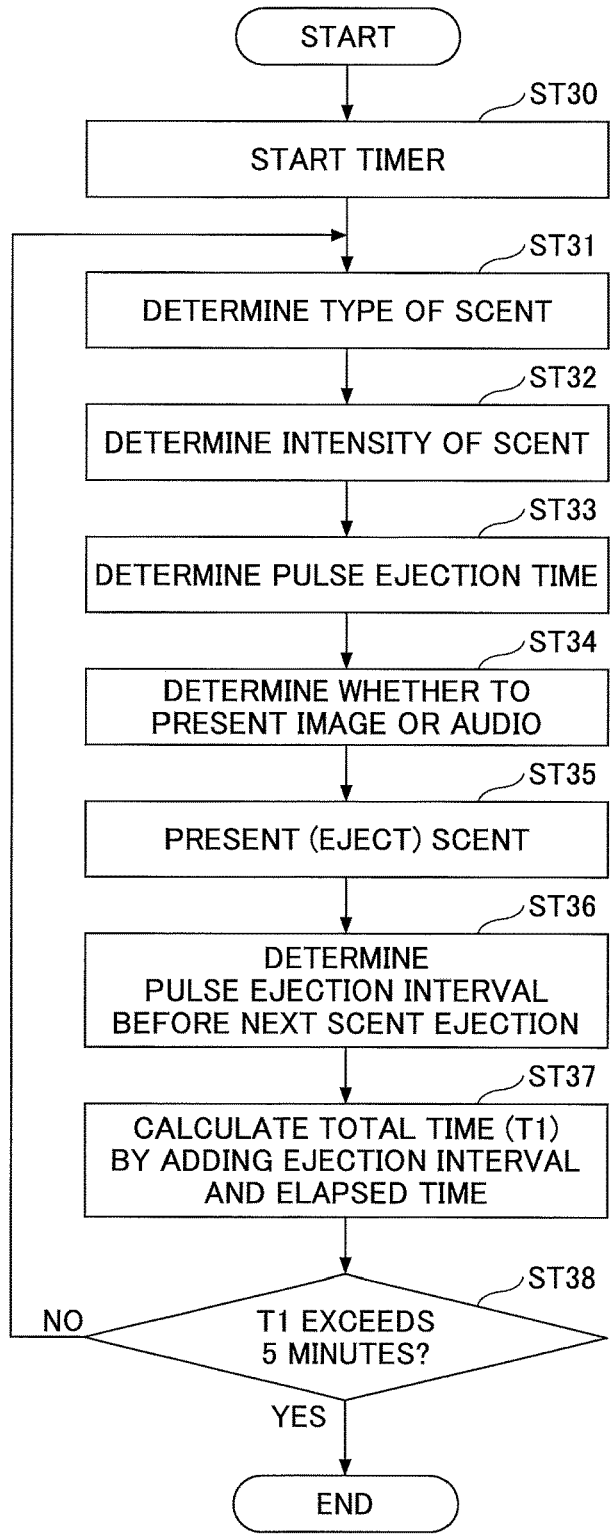
FIG. 5 is a flowchart showing another example process flow of the scent presentation method according to an embodiment of the present invention.

After the "type of scent" is determined by the determination process of FIG. 4, the process proceeds to step ST32 of FIG. 5 where the arithmetic processing unit 404 determines the "intensity of scent" corresponding to another one of the presentation conditions.

Figure 6:
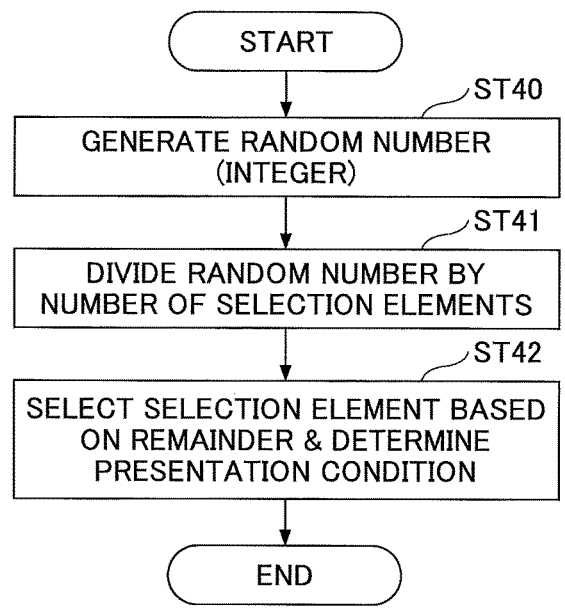
FIG. 6 is a flowchart showing a basic flow of a process for determining a presentation condition using a random number.

FIG. 6 is a flowchart showing a basic flow of a determination process for determining a presentation condition according to an embodiment of the present invention. The "intensity of scent" may be determined by implementing the determination process of FIG. 6, for example. Note that the process flow of FIG. 6 is basically the same as the process flow of FIG. 4 in that it involves determining the presentation condition based on a random number.

In step ST40, the arithmetic processing unit 404 of the information processing apparatus 400 controls the random number generating unit 404a to generate a random number. The random number to be generated may be any integer.

Then, in step ST41, the arithmetic processing unit 404 divides the generated random number by the number of selection elements that are provided as options for the "intensity of scent". Note that the number of selection elements provided as options for the "intensity of scent" is preferably a small number of about 2 to 10, for example.

Then, in step ST42, the arithmetic processing unit 404 selects a selection element based on the remainder obtained by dividing the random number by the number of selection elements to determine the presentation condition. To implement such a process, the remainder values are associated with the corresponding selection elements.

After the "intensity of scent" is determined by the above determination process of FIG. 6, the process proceeds to step ST33 of FIG. 5 where the "pulse ejection time" of the scent is determined. Note that the determination process of FIG. 6 may similarly be implemented to determine the "pulse ejection time" in step ST33. Note that if the "pulse ejection time" of a scent is too long, the user is more likely to become adapted to the scent. Accordingly, pulse ejection times that are short enough to prevent adaptation (e.g., pulse ejections times less than or equal to 1 sec) are preferably provided as selection elements for the "pulse ejection time".

After the "pulse ejection time" is determined in step ST33, the arithmetic processing unit 404 proceeds to step ST34 where it determines whether to present an image and/or audio associated with the type of scent determined in step ST31. In step ST34, the determination process using a random number as shown in FIG. 6 may be implemented, or the above presentation condition may be set up in advance by the administrator K or the user H, for example. The presentation condition of whether to present an image and/or audio associated with the selected scent may be set up in advance, in a case where the olfactory capabilities of the user appear to have improved, for example. By presenting a randomly selected type of scent to the user without an associated image and/or audio, the degree of improvement of the olfactory capabilities of the user may be determined, for example. Also, by presenting no image or audio associated with the type of scent selected, the user may be able to concentrate on smelling the scent and thereby further improve his/her olfactory capabilities, for example.

Then, in step ST35, the arithmetic processing unit 404 sends the presentation conditions determined by the above process steps to the control unit 210 of the scent presentation apparatus 200 and controls the scent presentation apparatus 200 to present the scent to the user H. Also, if it is determined in step ST34 that an image and/or audio associated with the scent is to be displayed/generated, the arithmetic processing unit 404 sends the corresponding image information and/or audio information associated with the scent to the control unit 301 of the tablet terminal 300.

After the scent is presented (ejected) in step ST35, the arithmetic processing unit 404 proceeds to step ST36 where it determines the "pulse ejection interval" between the present scent ejection and a next scent ejection. Note that the process of determining the "pulse ejection interval" in step ST36 may also be implemented by the determination process of FIG. 6, and as such, descriptions thereof are omitted.

Then, in step ST37, the arithmetic processing unit 404 calculates a total time T1 by adding the "pulse ejection interval" and the time elapsed from the start of the scent presentation process. Then, in step ST38, the arithmetic processing unit 404 determines whether the total time T1 exceeds the predetermined time period (e.g., 5 minutes) that has been set up in advance as the scent presentation period. If the total time T1 does not exceed the predetermined time period (NO in step ST38), the arithmetic processing unit 404 returns to step ST31 and repeats the above determination process for determining the presentation conditions for presenting a next scent. If the total time T1 exceeds the predetermined time period (YES in step ST38), the arithmetic processing unit 404 ends the scent presentation process.

Note that the processes of steps ST32, ST33, and ST36, do not necessarily have to be implemented by the determination process using a random number as shown in FIG. 6. For example, in some embodiments, certain values may be set up in advance for the "intensity of scent", the "pulse ejection time", and/or the "pulse ejection interval", and fine adjustments may be made to these values to suit each individual user.

[Example Application]

In the following, an example application of the present invention is described. Note, however, that applications of the present invention are not limited to this example.

In the present example application, an experiment that involved performing an olfaction improving treatment on test subjects was conducted using the scent presentation method, the scent presentation apparatus, and the olfaction improving apparatus according to the above-described embodiments of the present invention.

In the present experiment, the olfaction improving treatment was performed on 5 test subjects. The test subjects consisted of 5 women at an average age of 66.7±8.78 years old. All of the 5 test subjects were patients experiencing some olfactory impairment, such as difficulty in perceiving scents.

The olfaction improving apparatus 1 as shown in FIG. 1 was used in the present experiment, and the olfactory display (FJMC developed by Keio University) that is capable of ejecting a scent through pulse ejection as described above was used as the scent presentation apparatus 200. The olfactory display uses a Bubble Jet head to eject a scent through pulse ejection. Further, the olfactory display includes a large tank with 255 minute holes and small tanks with 127 minute holes, and is capable of controlling the ejection quantity of a scent by controlling the number of holes from which a scent is simultaneously ejected from each tank. More specifically, the olfactory display is capable of adjusting the ejection quantity to 256 different levels (0-255) for the large tank or 128 different levels (0-127) for the small tank.

Also, four tanks each filled with four different scents were installed in a cartridge. The four different scents include iso-amyl acetate as the scent of bananas, peppermint oil as the scent of mint, lavender oil as the scent of lavender, and phenyl ethyl alcohol as the scent of roses. In the present example, the banana scent was filled in the large tank, and the other scents were filled in the small tanks.

In the olfaction improving treatment of the present example, first, a detection threshold test was conducted to measure the detection threshold of a test subject. Then, based on the detection threshold measured for the test subject, the intensity of scent as a presentation condition to be applied in a subsequent olfaction improving treatment was set up for the test subject, and the olfaction improving treatment was conducted. Note that in the following descriptions, a scent may also be referred to as "smell".

In the detection threshold test, a test subject was asked to sit in a chair, and the scent presentation apparatus 200 (FJMC) and the tablet terminal 300 were placed on top of a desk in front of the test subject. The touch panel of the terminal apparatus 300 was used to implement operations relating to the detection threshold test (application). Note that the user H in FIG. 1 corresponds to the test subject in the present example, and the administrator K corresponds to the person conducting the present experiment. In the present example, it is assumed that the olfaction improving apparatus 1 is configured such that the user H can operate the tablet terminal 300 to go through the detection threshold test and the olfaction improving treatment in one sitting.

(Detection Threshold Test)

In the following, the detection threshold test is described in detail.

In the detection threshold test, the minimum intensity at which the test subject is able to detect a scent is measured, and the minimum intensity is determined to be the detection threshold for the scent. The scents used in the present test included a banana scent, a mint scent, a lavender scent, and a rose scent. The detection threshold test was carried out by emitting the banana scent, the mint scent, the lavender scent, and the rose scent in the above recited order. The intensity of scent was controlled by varying the ejection quantity of the scents in increments of 10. That is, with respect to the banana scent stored in the large tank, the ejection quantity was adjusted to vary in increments of 10 within the range of 10-250 (based on the number of holes in the tank), and with respect to the other scents stored in the small tanks, the ejection quantity was adjusted to vary in increments of 10 within the range of 10-120 (based the number of holes in the tank).

Also, in the detection threshold test, a triple-choice comparison method was used where, in each trial, ejections were performed three times (one being scented and the other two being scentless), and the test subject was asked to indicate at which time, out of the three times, a smell could be detected. The scent was presented in ascending order, from the weakest to the strongest. The test subject was required to correctly detect the scented ejection over two consecutive trials, and if successful, the intensity of the scent presented at the time was determined to be the detection threshold of the test subject. If the test subject made the wrong choice, the intensity of scent was raised one step higher, and the same test procedures were performed. Note that the intensity of scent at the start of the detection threshold test was set to 10, and the test was continued until the test subject successfully detected the scent over two consecutive trials, or until the intensity reached 250 (for banana) or 120 (for mint, lavender, and rose) and the test subject was still unable to correctly detect the scent.

The pulse ejection time of the scent presentation was set to one of 100 ms, 200 ms, or 300 ms according to the olfactory capabilities of the test subject. Because the pulse ejection time was set to such a relatively short time period, the scent presentation timing was signaled to the test subject by a countdown display on the touch panel and audio information from the audio generating unit 303 to assist the test subject in smelling the scent.

Figure 7:
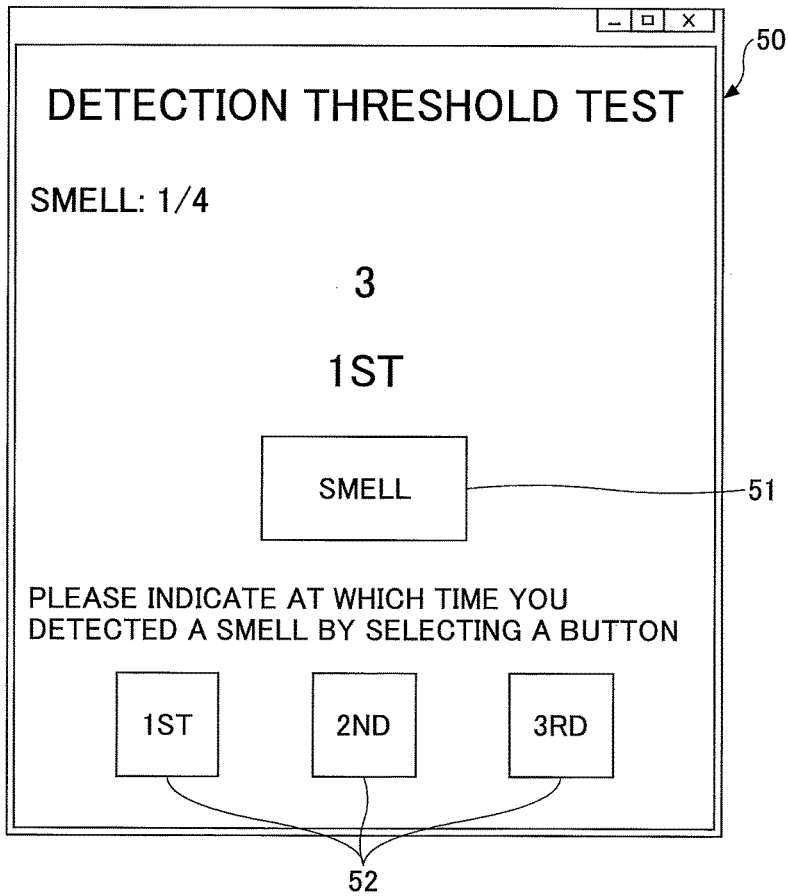
FIG. 7 is a diagram showing an example display of guidance information for a detection threshold test.

Note that the test subject operated the touch panel of the tablet terminal 300 to manipulate the guidance information displayed on the touch panel while undergoing the detection threshold test. FIG. 7 is a diagram showing an example of a display screen of the touch panel of the table terminal 300 displaying guidance information during the detection threshold test.

The display component "SMELL: ¼" at the upper left corner of the screen 50 shown in FIG. 7 indicates which of the four types of scents is currently being tested. The display component "1ST" at the center of the screen 50 indicates whether an upcoming ejection corresponds to a first, a second, or a third ejection. In the present example, three ejections including one scented ejection and two scentless ejections were presented to the test subject in random order. Then, the test subject was asked to indicate at which time a scent could be detected. The display component indicating a number "3" at the upper portion of the screen 50 represents a countdown number for enabling the test subject to adjust his/her inhalation timing according to the scent presentation timing. Also, the screen 50 includes a "SMELL" button 51 to be pressed by the test subject. When the test subject presses the "SMELL" button 51, the countdown number being displayed changes from 3, 2, 1, to 0, and a scent is presented to the test subject at the time the countdown number is switched to 0. Further, the screen 50 includes three buttons 52 indicated as "1ST", "2ND", and "3RD". After three scent presentations (ejections), the test subject selects (touches) one of the three buttons 52 to indicate at which time the test subject was able to detect a scent.

By conducting the above detection threshold test, the minimum intensity at which the test subject is able to detect a scent may be determined, and such information may be used in performing the olfaction improving treatment on the test subject. That is, the intensity of a scent to be presented during the olfaction improving treatment may be adjusted according to the detection threshold measurement obtained for the test subject. In the following descriptions, specific procedures of the olfaction improving treatment are described. Note that in the example described below, it is assumed that the "intensity of scent" for the test subject is already determined based on detection threshold measurements obtained by conducting the above-described detection threshold test on the test subject.

(Olfaction Improving Treatment)

In the olfaction improving treatment conducted in the present experiment, four types of scents were presented to a test subject, and the test subject was asked to continue smelling each scent for a predetermined time period.

In the present experiment, 5 patients (test subjects) were asked to undergo the olfaction improving treatment once a week for a period of 4 weeks. The patients are identified as "patient 1", "patient 2", "patient 3", "patient 4", and "patient 5" below.

Note, however, that patient 3 was not able to participate in the first week of the experiment due to illness. As such, the olfaction improving treatment was conducted on patient 3 only 3 times.

In the olfaction improving treatment, each test subject was asked to sit in a chair, and the scent presentation apparatus 200 (FJMC) and the tablet terminal 300 were placed on top of a desk in front of the test subject as shown in FIG. 1. Also, the touch panel 302 of the tablet terminal 300 was used to implement operations relating to the olfaction improving treatment (application).

Parameters (presentation conditions) for presenting a scent during the olfaction improving treatment include type of scent, intensity of scent, treatment time, pulse ejection time, and pulse ejection interval before a next scent ejection.

Among the above presentation conditions, the type of scent was set up to vary randomly based on a random number, and the intensity of scent and the pulse ejection time were set to suitable values according to the detection thresholds and the olfactory capabilities of each test subject. The other presentation conditions were set to fixed values.

The pulse ejection time was set up according to the olfactory capabilities of each test subject. Specifically, the pulse ejection time was set to 300 ms for patient 1, patient 2, and patient 3; and the pulse ejection time was set to 100 ms for patient 5. For patient 4, the pulse ejection time was set to 300 ms the first week and the second week; and the pulse ejection time was set to 200 ms the third week and the fourth week.

The intensity of scent was set to a value obtained by adding 30 to the detection threshold measured by the detection threshold test conducted immediately before the olfaction improving treatment such that the test subject would be able to more easily detect the scent to be presented. However, in the case where the value obtained by adding 30 to the detection threshold of the test subject for a scent exceeded the maximum intensity, the intensity of scent was set to the maximum intensity of 250 if the scent was stored in the large tank or 120 if the scent was stored in the small tank.

The olfaction improving treatment involved performing three sets of scent presentations, the first set being performed for 4 minutes, and the second and third sets being performed for 5 minutes each for a total presentation time of 14 minutes. A break (interval) was provided in between the sets in order to prevent scent adaptation and fatigue from continuously smelling scents.

Further, in the first set, the test subject was required to continuously smell the four different types of scents in a predetermined order, each for one minute; and in the second and third sets, the test subject was required to continuously smell the four different types of scents that were randomly switched every minute.

Note that in the first set, the predetermined order in which the four types of scents were presented to the test subject was the same as the order in which the four types of scents were presented in the detection threshold test (i.e., banana, mint, lavender, and rose). The scent presentation was performed once every 8 seconds, and the pulse ejection time of one scent presentation was set up to be the same as the pulse ejection time used in the detection threshold test conducted for each test subject. Further, as with the detection threshold test, the scent presentation timing was signaled to the test subject by audio and the like to assist the test subject in smelling the scent being ejected.

In the second and third set of scent presentations performed in the present experiment, the scent presentation method involving randomly determining the type of scent to be presented based on a random number as described above with reference to FIG. 3 and FIG. 4 was implemented.

Figure 8:
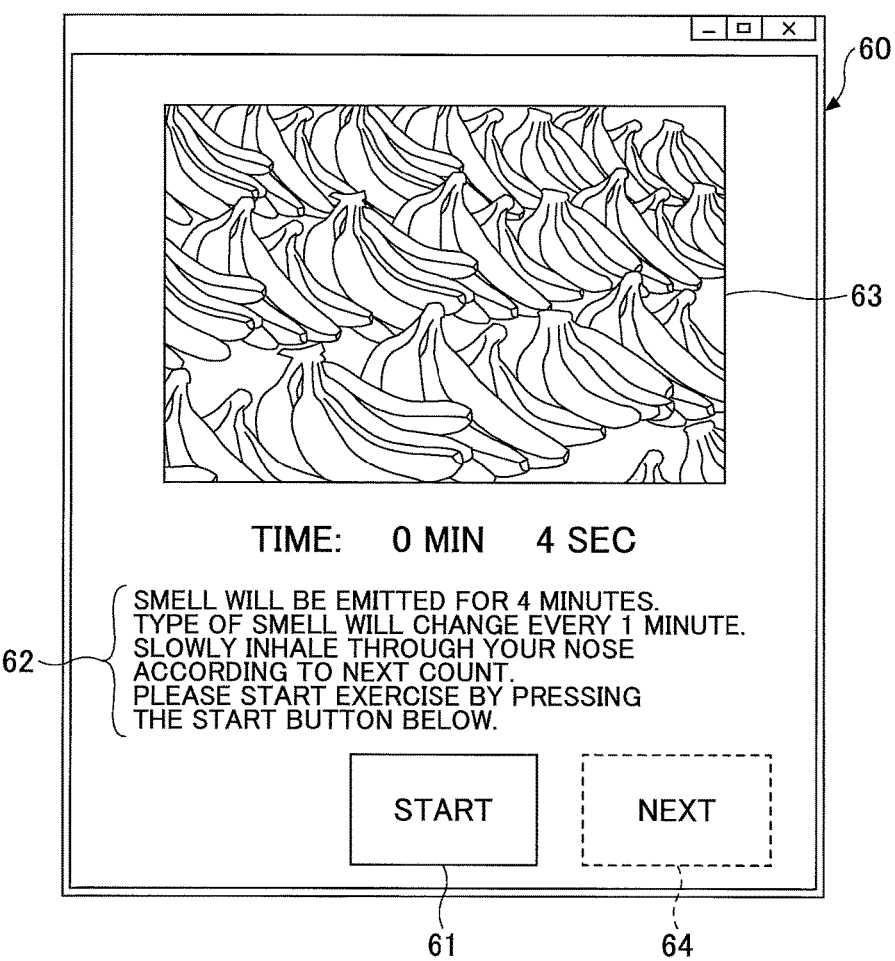
FIG. 8 is a diagram showing an example display of guidance information for an olfaction improving treatment.

Also, like the detection threshold test, the olfaction improving treatment was performed by having the test subject manipulate the guidance information displayed on the touch panel of the tablet terminal 300. FIG. 8 is a diagram showing an example of a display screen of the touch panel of the tablet terminal 300 displaying guidance information for implementing the olfaction improving treatment.

The olfaction improving treatment may be started when a "START" button 61 displayed at a bottom portion of the screen 60 shown in FIG. 8 is pressed. The display component "TIME: 0 MIN 4 SEC" at the center of the screen 60 indicates the time elapsed from the start of the olfaction improving treatment. Also, a guidance message 62 is displayed below the display component indicating the elapsed time. The guidance message 62 provides a description of the olfaction improving treatment to the test subject.

Further, a scent image 63 associated with the scent being ejected from the scent presentation apparatus 200 is displayed at the upper portion of the screen 60. Displaying the scent image 63 may make it easier for the test subject to recognize the scent being presented. For example, in the case where the banana scent is presented to the test subject, an image of bananas may be displayed as the scent image 63 as shown in FIG. 8. Note that the scent image 63 is not displayed before the "START" button 61 is pressed. When a given set of scent presentations is completed, a transition button 64 indicated as "NEXT" is displayed at the right side of the "START" button 61. By pressing the transition button 64, the olfaction improving treatment may proceed to the next set of scent presentations. The above operations may be continued until scent presentation is performed for the predetermined presentation time of 14 minutes, for example.

Note that in the second and third sets of scent presentations where the type of scent to be presented is randomly determined based on a random number, the test subject may concentrate on trying to recognize the scent being presented, and in this way, olfactory capabilities of the test subject may be improved, maintained, or enhanced, for example. Also, in a preferred embodiment, the second and third sets of scent presentations are set up such that the presentation condition of whether to present the image and/or audio associated with the scent being presented is randomly determined based on a random number, for example. Such a setup may be particularly preferred for presenting scents to a test subject whose olfactory capabilities appear to be improving, for example.

<Experimental Results>

FIGS. 9A-9E are tables indicating the results of conducting the above-described olfaction improving treatment on the 5 patients (test subjects) once a week for a period of for 4 weeks. FIGS. 9A-9E indicate values obtained by converting the detection thresholds of the test subjects into ejection quantities based on the detection thresholds and the pulse ejection time. Specifically, the ejection quantities were obtained using the above equation (1).

Note that FIG. 9A shows the results for patient 1, FIG. 9B shows the results for patient 2, FIG. 9C shows the results for patient 3, FIG. 9D shows the results for patients 4, and FIG. 9E shows the results for patient 5. Note that in FIGS. 9A-9E, "UNMEASURABLE" represents a case where the detection threshold of the patient could not be measured. The numerical values represent ejection quantities in microliters [μL].

The experimental results obtained for each of the patients are discussed below.

It can be appreciated from FIG. 9A that for patient 1, the detection thresholds for mint and lavender progressively decreased as the olfaction improving treatment was repeated. It can be appreciated from FIG. 9B that for patient 2, the detection thresholds for all of the scents progressively decreased as the olfaction improving treatment was repeated, and in particular, the detection threshold for banana significantly decreased. It can be appreciated from FIG. 9C that for patient 3, the detection thresholds for the scents other than rose decreased. It can be appreciated from FIGS. 9D and 9E that the detection thresholds of patient 4 and patient 5 were much lower than those of the other three patients and they tended to fluctuate up and down. Moreover, considering the fact that patient 4 and patient 5 were able to detect all of the scents despite the relatively short pulse ejection time set up for the olfaction improving treatment, it can be concluded that patient 4 and patient 5 had no problems in detecting the four types of scents presented in the present experiment.

In the following, it is assumed that patient 1, patient 2, and patient 3 that were subject to the olfaction improving treatment with the pulse ejection time set to 300 ms belong to group L with lower olfactory capabilities; and patient 4 and patient 5 that were subject to the olfaction improving treatment with the pulse ejection time set shorter than 300 ms belong to group H with higher olfactory capabilities.

With respect to the patients belonging to group L, the detection thresholds for at least one type of scent decreased as the olfaction improving treatment was repeated, and the patients also reported experiencing improved olfaction in their daily lives. On the other hand, with respect to the patients belonging to group H, no substantial decrease in the detection thresholds were observed, and the patients experienced no particular change in olfaction in their daily lives.

It can be appreciated from the above that the olfaction improving treatment was effective for the patients with low olfactory capabilities. The decrease in the detection thresholds of the patients may be attributed to the effects of olfactory stimulation through pulse ejection that was performed in olfaction improving treatment. That is, the scent presentation apparatus (olfactory display) used in the olfaction improving treatment is capable of instantaneous scent control through pulse ejection. Because the patients were not accustomed to such instantaneous changes in olfactory stimulation in their daily lives, the olfaction sensory cells of the patients may have been stimulated by the olfaction improving treatment to thereby cause the decrease in the detection thresholds.

As described above, the scent presentation method, the scent presentation apparatus, and the olfaction improving apparatus including the scent presentation apparatus according to embodiments of the present invention are configured to determine a presentation condition based on a random number that has been generated.

In the application example described above, one presentation condition (type of scent) was randomly altered in presenting a scent to test subjects. As a result, improvements in olfactory capabilities could be observed with respect to test subjects with low olfactory capabilities. Also, by randomly altering other presentation conditions and causing test subjects to concentrate on trying to recognize a scent being presented, olfactory capabilities may potentially be maintained or enhanced even with respect to test subjects with no substantial olfactory impairments, for example. In particular, it is believed that olfactory capabilities may potentially be enhanced by randomly altering the intensity of scent.

Note that the scent presentation method, the scent presentation apparatus, and the olfaction improving apparatus according to embodiments of the present invention may be applied to various situations, such as to enable engagement in hobbies and entertainment involving olfaction, for example. Further, embodiments of the present invention may be applied in the context of training professionals that rely on their olfactory capabilities, such as sommeliers and perfumers, for example.

Further, embodiments of the present invention are not limited to a scent presentation method and a scent presentation apparatus for improving, maintaining, or enhancing olfactory capabilities. That is, the present invention is highly versatile and can be used in various applications and industries including scent presentation methods and scent presentation apparatuses used in entertainment, for example.

Note that by applying embodiments of the present invention in the field of entertainment, a variety of diverse environments may be created, for example.

Although the present invention has been described above with respect to certain illustrative embodiments, the present invention is not limited to these embodiments, and various variations and modifications may be made without departing from the scope of the present invention.

What is claimed is:

1. An olfaction improvement method comprising:
   determining a detection threshold at which a test subject is able to detect a scent selected from among a plurality of scents by
      presenting the scent by pulse ejecting the scent for a specified time interval between from about 100 ms to about 300 ms to vary the intensity of the scent,
      detecting an operation of a terminal device by the test subject upon detection of the scent by the test subject, and
      setting the intensity of the scent detected by the test subject over at least two consecutive trials as the detection threshold of the test subject for each scent from among the plurality of scents, wherein the plurality of scents are selected and presented in a predetermined sequence;
   generating a random number to randomly determine a presentation sequence of the plurality of scents;
   determining presentation conditions that include the intensity of the scent and the pulse ejection duration of the scent based on the detection threshold of the test subject;
   presenting the scent through pulse ejection based on the determined presentation condition; and
   altering the presentation conditions by reducing the intensity of the scent, the pulse ejection duration of the scent, or both the intensity of the scent and the pulse ejection duration of the scent relative to the detection threshold of the test subject when presenting the scent at a subsequent time, wherein
   the scent is pulse ejected by a fluid ejection device.

2. The olfaction improvement method according to claim 1, wherein
   the presentation sequence is determined based on a remainder obtained by dividing the generated random number by a number of selection elements that are provided as options for the presentation condition.

3. The olfaction improvement method according to claim 2, wherein
   the presentation conditions further include a pulse ejection interval before presenting a next randomly selected scent.

4. A scent presentation apparatus comprising:
   a control unit; and
   a memory storing program instructions that cause the control unit to
      determine a detection threshold at which the test subject is able to detect a scent selected from among a plurality of scents by presenting the scent by pulse ejecting the scent for a specified time interval between from about 100 ms to about 300 ms to vary the intensity of the scent, detecting an operation of a terminal device by the test subject upon detection of the scent by the test subject, and setting the intensity of the scent detected by the test subject over at least two consecutive trials as the detection threshold of the test subject for each scent from among the plurality of scents, wherein the plurality of scents are selected and presented in a predetermined sequence;

generate a random number to determine a random presentation sequence of the plurality of scents;

determine presentation conditions that include at least one of the intensity of the scent and the pulse ejection duration of the scent based on the detection threshold of the test subject;

presenting the scent through pulse ejection based on the determined presentation condition; and alter the presentation conditions by reducing the intensity of the scent, the pulse ejection duration of the scent, or both the intensity of the scent and the pulse ejection duration of the scent relative to the detection threshold of the test subject when presenting the scent at a subsequent time; and an ejection unit configured to pulse eject the scent.

5. The scent presentation apparatus according to claim 4, wherein execution of the program further causes the control unit to:

control an indicator to signal execution of the pulse ejection.

6. An olfaction improving apparatus comprising:

a scent presentation apparatus;

a display terminal; and an information processing apparatus that includes a control unit; and a memory storing program instructions that cause the control unit to:

determine a detection threshold at which the test subject is able to detect a scent selected from among a plurality of scents by presenting the scent by pulse ejecting the scent for a specified time interval between from about 100 ms to about 300 ms to vary the intensity of the scent, detecting an operation of a terminal device by the test subject upon detection of the scent by the test subject, and setting the intensity of the scent detected by the test subject over at least two consecutive trials as the detection threshold of the test subject for each scent from among the plurality of scents, wherein the plurality of scents are selected and presented in a predetermined sequence;

generate a random number to determine a random presentation sequence of the plurality of scents;

determine presentation conditions that include the intensity of the scent and the pulse ejection duration of the scent based on the detection threshold of the test subject;

presenting the scent through pulse ejection based on the determined presentation condition; and altering the presentation conditions by reducing the intensity of the scent, the pulse ejection duration of the scent, or both the intensity of the scent and the pulse ejection duration of the scent relative to the detection threshold of the test subject when presenting the scent at a subsequent time, wherein the scent is pulse ejected by a fluid ejection device included in the scent presentation apparatus the display terminal is configured to display an image on a display screen, the image being associated with the scent.

7. The olfaction improving apparatus according to claim 6, wherein execution of the program further causes the control unit to:

control an audio generating unit provided in the display terminal to generate audio information that is associated with the scent.

8. The olfaction improving apparatus according to claim 6, wherein the display terminal displays guidance information for operating the display terminal.

* * * * *